United States Patent
Ziegler et al.

(10) Patent No.: US 7,863,417 B2
(45) Date of Patent: Jan. 4, 2011

(54) TRIPEPTIDES AND DERIVATIVES THEREOF FOR COSMETIC APPLICATION IN ORDER TO IMPROVE SKIN STRUCTURE

(75) Inventors: Hugo Ziegler, Witterswil (CH); Marc Heidl, Grenzach-Wyhlen (DE); Dominik Imfeld, Münchenstein (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/555,994

(22) PCT Filed: May 7, 2004

(86) PCT No.: PCT/CH2004/000278

§ 371 (c)(1),
(2), (4) Date: Nov. 13, 2006

(87) PCT Pub. No.: WO2004/099237

PCT Pub. Date: Nov. 18, 2004

(65) Prior Publication Data

US 2007/0099842 A1   May 3, 2007

(30) Foreign Application Priority Data

May 8, 2003   (CH) .................................. 0807/03

(51) Int. Cl.
*C07K 5/08* (2006.01)
(52) U.S. Cl. .......................... 530/331; 514/18
(58) Field of Classification Search .................. 530/331; 514/18
See application file for complete search history.

(56) References Cited

U.S. PATENT DOCUMENTS

| | | | |
|---|---|---|---|
| 4,389,342 A * | 6/1983 | Reinhard ..................... | 530/327 |
| 4,686,282 A * | 8/1987 | Hahn ......................... | 530/327 |
| 4,929,601 A * | 5/1990 | Brunetti et al. ............... | 514/18 |
| 5,028,593 A * | 7/1991 | Nishioka .................... | 514/18 |
| 5,593,849 A * | 1/1997 | Roy .......................... | 435/7.33 |
| 6,262,017 B1 * | 7/2001 | Dee et al. .................... | 514/2 |
| 6,333,167 B1 * | 12/2001 | Quinet et al. ................ | 435/23 |

2002/0051988 A1   5/2002   Gilchrest et al.

FOREIGN PATENT DOCUMENTS

| FR | 2 740 453 A1 | 4/1997 |
|---|---|---|
| FR | 2 810 323 A1 | 12/2001 |
| JP | 53-36477 B | 10/1978 |
| WO | WO 89/12441 | 12/1989 |
| WO | WO 02/069884 A2 | 9/2002 |

OTHER PUBLICATIONS

International Search Report for PCT/CH2004/000278, mailed Aug. 2, 2004.

* cited by examiner

*Primary Examiner*—David Lukton
(74) *Attorney, Agent, or Firm*—Hoffmann & Baron, LLP

(57) ABSTRACT

The invention relates to compounds and to the cosmetically acceptable salts thereof, which correspond to general formula (I), wherein: $R^1$ represents H, $-C(O)-R^6$, $-SO_2-R^6$ or $-C(O)-XR^6$; $R^2$ and $R^4$, independent of one another, represent $(CH_2)_n-NH_2$ or $(CH_2)_3-NHC(NH)NH_2$; n equals 1–4; $R^3$ represents linear or branched $C_1$-$C_4$ alkyl that is optionally substituted by hydroxy; $R^5$ and $R^6$, independent of one another, represent hydrogen, optionally substituted $(C_1$-$C_{24})$ alkyl, optionally substituted $C_2$-$C_{24}$ alkenyl, optionally substituted phenyl, optionally substituted phenyl-$C_1$-$C_4$ alkyl or 9-fluorenyl-methyl; X represents oxygen $(-O-)$ or $-NH-$; or $XR^5$ with $X=O$ also represents the esters of a-tocopherol, tocotrienol or retinol, with the provision that $R^1$ and $R^5$ do not represent hydrogen and X does not represent oxygen at the same time. The invention also relates to the production of the compounds of general formula (I) and to a cosmetically active composition that contains at least one compound of formula (I).

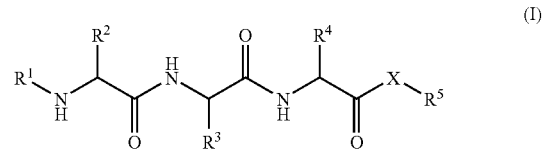

(I)

5 Claims, No Drawings

TRIPEPTIDES AND DERIVATIVES THEREOF FOR COSMETIC APPLICATION IN ORDER TO IMPROVE SKIN STRUCTURE

CROSS-REFERENCE TO RELATED APPLICATIONS

This application is the National Stage of International Application No. PCT/CH2004/000278, filed May 7, 2004, which claims the benefit of CH 807/03, filed May 8, 2003, the contents of which are incorporated by reference herein.

INTRODUCTION

It is known that endogenous (age-related) or exogenous (light-induced) aging leads to an irreversible degeneration of tissues, in particular of skin. These modifications result from a reduction of anabolic reactions (syntheses) and an increase of catabolic reactions (degradation) of collagen and elastin, the two main constituents of the skin matrix.

The synthesis reactions in the skin matrix are mostly regulated by polypeptides, so-called growth factors and cytokines. Among these peptides, TGFβ1 is one of the most important regulators involved in the synthesis reactions of this skin matrix. It is secreted in the matrix by keratinocytes and fibroblasts in a latent form and has to be activated in order to be recognized by the cell receptors and to be able to induce a biological response (collagen and elastin synthesis). Two forms of latent TGFβ1 are available:

a small, latent complex composed of 2 TGFβ-chains that are non-covalently bound to a so-called "latency associated protein" (LAP).

a large, latent TGFβ1-complex, in which the small, latent TGFβ1-complex is covalently bound (disulfide bonds) by the LAP to another, so-called "latent TGFβ binding protein" (LTBP). It has been found recently that in human skin this large, latent TGFβ1-complex is associated to fibrillin, a microfibril-forming molecule; these microfibrils are themselves bound to elastin. Thus, the large, latent TGFβ1-complex constitutes the greatest reservoir of latent TGFβ1 in skin.

There are several physiological mechanisms to activate TGFβ1. The main method in vivo is the activation of latent TGFβ1 by thrombospondin-1 (TSP-1), a protein secreted by the skin cells. This activation bases on the interaction between the LAP of the latent TGFβ1 and the tripeptide sequence RFK (Arg-Phe-Lys) of TSP-1, XFX (with X=basic amino acid) being the smallest sequence required for the activation of latent TGFβ1.

During the aging process the bioavailability and the TGFβ1 activity are reduced by a decreased genetic expression and a modified capacity of fixing to fibroblast receptors. These modifications cause weakened synthesis reactions of the elastin and collagen fibres. The degradation reactions in the skin matrix are mainly produced by proteolytic enzymes, the matrix proteinases (MMPs).

MMP-1 (or collagenase) and MMP-2 (or gelatinase A) secreted by skin fibroblasts are involved in the chrono-induced aging process. Their number increases in aging skin, leading to a modification of collagen and elastin fibres. In the photo-induced aging process the MMP-9 (or gelatinase B) and MMP-3 (leukocyte elastase) are involved. They are secreted by keratinocytes and or polynuclear neutrophils during UV-induced, inflammatory processes, whereby the elastin and collagen fibres are degraded and reduced (elastose).

Consequently, the decreased anabolism and the increased catabolism of the macromolecules in the skin matrix lead to an imbalance that is responsible for the appearing of the following clinical symptoms: skin atrophy, loss of the mechanical properties with relief and elasticity loss, skin flabbiness, deep mimic wrinkles, accelerated formation of wrinkles and streaks, and disappearance of the natural skin lines.

In order to prevent the above mentioned modifications and clinical symptoms, and to improve the appearance of the skin surface in particular by reducing the wrinkle depth and eliminating fine wrinkles, it would be sensible to apply substances capable of simultaneously exerting the following effects:

activation of the synthesis reactions in the skin matrix by stimulating the growth factor (TGFβ1) activity responsible for the anabolism of the macromolecules of the extracellular matrix reduction of the degradation reactions in the skin matrix by modulating the metalloproteinase activity responsible for the catabolism of the macromolecules in the extracellular matrix and protection of these components from the influence of these enzymes.

As collagen represents about 80% of the skin proteins, it is easily understandable that the smallest diminution of its tissue concentration may have considerable consequences for the mechanical and physiological properties of skin.

It has been surprisingly found that it is possible to synthesize cosmetically active tripeptides and derivatives thereof (hereinafter referred to as "compounds of the present invention") and topically applicable, cosmetic compositions against chrono- and photo-induced skin aging (anti-aging products), which may diffuse rapidly and in sufficient concentration through the cell membrane up to the intracellular site of action and produce a rapid and strong stimulation of collagen synthesis. This results from the capacity of the compounds of the present invention to activate the synthesis reactions in the skin matrix by specifically stimulating the growth factor TGFβ1 responsible for the anabolism of macromolecules in the skin matrix.

Therefore, the compounds of the present invention exert a stimulating effect on the extracellular matrix, which decisively influences the mechanical and physiological appearance of skin.

It could be shown that replacing the central amino acid in the tripeptide sequence RFK (Arg-Phe-Lys) of TSP-1 by an amino acid bearing an alkyl chain optionally substituted by hydroxy as a side chain, together with substituting the peptide with a penetration-enhancing, lipophilic group result in a quicker diffusion through the cell membrane up to the intracellular site of action in higher concentration and that the compounds of the present invention thus produce a quicker and stronger stimulation of collagen synthesis than the compound elaidyl-Lys-Phe-Lys corresponding to the state-of-the-art and described in the patent application FR 2810323 published on Dec. 21, 2001.

The present invention relates to tripeptides and tripeptide derivatives of general formula I

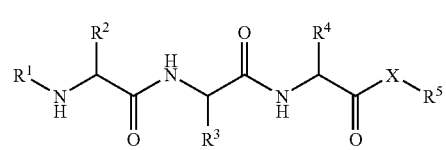

wherein
$R^1$ represents H, —C(O)—$R^6$, —SO$_2$—$R^6$ or —C(O)—X$R^6$ $R^2$ and $R^4$, independent of one another, represent $(CH_2)_n$—$NH_2$ or $(CH_2)_3$—$NHC(NH)NH_2$, n equals 1-4, $R^3$ represents linear or branched $C_1$-$C_4$-alkyl that is optionally substituted by hydroxy, $R^5$ and $R^6$, independent of one another, represent hydrogen, optionally substituted $(C_1$-$C_{24})$-alkyl, optionally substituted $C_2$-$C_{24}$-alkenyl, optionally substituted phenyl, optionally substituted phenyl-$C_1$-$C_4$-alkyl or 9-fluorenylmethyl, X represents oxygen (—O—) or —NH—; or $XR^5$ with X=O also represents the esters of α-tocopherol, tocotrienol or retinol, as racemates or as pure enantiomers, as well as the salts thereof for application as cosmetic actives.

The above used, general terms are defined as follows: alkyl comprises linear as well as branched alkyl groups. Examples thereof are methyl, ethyl, propyl, n-butyl, n-pentyl, n-hexyl, n-heptyl, n-octyl, n-nonyl, n-undecanyl, n-dodecanyl, n-tridecanyl, n-hexadecanyl, n-heptadecanyl, n-octadecanyl or n-nonadecanyl as unbranched residues and isopropyl, tert.butyl, isobutyl, sec.butyl, isoamyl as branched residues. $R^5$ and $R^6$, as optionally substituted alkyl and independent of one another, preferably represent $(C_2$-$C_{24})$-alkyl, preferably $(C_3$-$C_{18})$-alkyl.

Alkenyl has the denotation of a mono- or poly-unsaturated, optionally substituted alkyl group, such as e.g. 8(Z)-heptadecenyl, 8(Z),11(Z)-heptadecadienyl, 4(Z),7(Z),10(Z),-13(Z)-nonadecatetraenyl, 8(Z)-11-hydroxyoctadecenyl.

α-Tocopheryl means (D)-, (L)- or (DL)-2,5,7,8-tetramethyl-2-(4',8',12'-trimethyltridecyl)-6-chromanyl, tocotrienyl means any isomer of 2,5,7,8-tetramethyl-2-(4',8',12'-trimethyl-3',7',11'-tridecatrienyl)-6-chromanyl and retinyl means 3,7-dimethyl-9-(2,6,6-trimethyl-1-cyclohexenyl)-2,4,6,8-nonatetraen-1-yl.

The compounds of formula (I) together with acids can form mono- or polyvalent, homogeneous or mixed salts, e.g. with inorganic acids, such as hydrochloric acid, hydrobromic acid, sulfuric acid or phosphoric acid; or with appropriate carboxylic acids, e.g. aliphatic mono- or dicarboxylic acids, such as formic acid, acetic acid, trifluoroacetic acid, trichloroacetic acid, propionic acid, glycolic acid, succinic acid, fumaric acid, malonic acid, maleic acid, oxalic acid, phthalic acid, citric acid, lactic acid or tartaric acid; or with aromatic carboxylic acids, such as benzoic acid or salicylic acid; or with aromatic-aliphatic carboxylic acids, such as mandelic acid or cinnamic acid; or with heteroaromatic carboxylic acids, such as nicotinic acid; or with aliphatic or aromatic sulfonic acids, such as methanesulfonic acid or toluenesulfonic acid. Dermatologically tolerated salts are preferred.

The general formula (I) includes all the possible isomeric forms as well as mixtures thereof, e.g. racemic mixtures and mixtures of rotamers.

Compounds of general formula I, wherein $R^1$ means —C(O)—$R^6$, $R^2$ and $R^4$ mean $(CH_2)_n$—$NH_2$, $R^3$ means linear or branched $C_1$-$C_4$-alkyl, $R^5$ means hydrogen, $(C_1$-$C_{24})$-alkyl, $(C_2$-$C_{24})$-alkenyl, phenyl, phenyl-$(C_1$-$C_4)$-alkyl, preferably hydrogen, and $R^6$ means $(C_1$-$C_{24})$-alkyl or $C_2$-$C_{24}$-alkenyl are preferred.

Furthermore, the following compounds are preferred:

Elaidoyl-Lys-Val-Lys-OH
Elaidoyl-Lys-Thr-Lys-OH
Palm-Lys-Thr-Lys-OH
Palm-Lys-Val-Lys-OH
Palm-Orn-Val-Lys-OH
Palm-Orn-Val-Dab-OH
Palm-Orn-Val-Dap-OH
Palm-Dab-Val-Lys-OH
Palm-Dab-Val-Dab-OH
Palm-Dab-Val-Dap-OH
Palm-Dap-Val-Lys-OH
Palm-Dap-Val-Dab-OH
Palm-Dap-Val-Dap-OH
Palm-Arg-Val-Lys-OH
Palm-Arg-Val-Dab-OH
Palm-Arg-Val-Dap-OH
Palm-Lys-Val-Lys-OH
Palm-Lys-Val-Orn-OH
Palm-Lys-Val-Dab-OH
Palm-Lys-Val-Dap-OH
Palm-Lys-Val-Arg-OH
Palm-Lys-Leu-Lys-OH
Palm-Lys-Ile-Lys-OH
Palm-Lys-Ile-Dab-OH
Palm-Lys-Nva-Dab-OH
Palm-Lys-tBuGly-Dab-OH
Palm-Lys-Leu-Dab-OH
Palm-Lys-Ile-Dap-OH
Palm-Lys-Nva-Dap-OH
Palm-Lys-tBuGly-Dap-OH
Palm-Lys-Leu-Dap-OH
Palm-Lys-Nle-Lys-OH
Palm-Lys-Ala-Lys-OH
Palm-Lys-Ser-Lys-OH
Palm-Lys-Hse-Lys-OH
Palm-Arg-Val-Arg-OH
Pentadecanoyl-Lys-Val-Dab-OH
Pentadecanoyl-Lys-Val-Dap-OH
Heptadecanoyl-Lys-Val-Dab-OH
Heptadecanoyl-Lys-Val-Dap-OH
Myristoyl-Lys-Val-Lys-OH
Myristoyl-Lys-Val-Dab-OH
Myristoyl-Lys-Val-Dap-OH
Lauroyl-Lys-Val-Lys-OH
Caprinoyl-Lys-Val-Lys-OH
Stearoyl-Lys-Val-Lys-OH
Stearoyl-Lys-Val-Dab-OH
Stearoyl-Lys-Val-Dap-OH
Oleolyl-Lys-Val-Lys-OH
Palm-Lys-Val-Dab-OMe
Palm-Lys-Val-Dab-OOctyl
Palm-Lys-Val-Dab-OCetyl
Palm-Lys-Val-Dab-$NH_2$
Palm-Lys-Val-Dab-NHBu
Palm-Lys-Val-Dab-NHOctyl
Palm-Lys-Val-Dab-NHCetyl
Palm-Lys-Val-Dap-OMe
Palm-Lys-Val-Dap-OOctyl
Palm-Lys-Val-Dap-OCetyl
Palm-Lys-Val-Dap-$NH_2$
Palm-Lys-Val-Dap-NHBu
Palm-Lys-Val-Dap-NHOctyl
Palm-Lys-Val-Dap-NHCetyl
$C_{14}H_{29}$—NH—CO-Lys-Val-Lys-OH
$C_{14}H_{29}$—NH—CO-Dab-Val-Dab-OH
$C_{14}H_{29}$—NH—CO-Lys-Ile-Dab-OH
$C_{14}H_{29}$—NH—CO-Lys-Val-Dap-OH
$C_{14}H_{29}$—NH—CO-Arg-Val-Arg-OH
$C_{14}H_{29}$—NH—CO-Dab-Val-Dap-OH
$C_{14}H_{29}$—NH—CO-Lys-Ile-Dap-OH
$C_{14}H_{29}$—NH—CO-Lys-Val-Dab-OH
$C_{14}H_{29}$—NH—CO-Dap-Val-Dap-OH $C_{16}H_{33}$—NH—CO-Lys-Val-Lys-OH
$C_{18}H_{37}$—NH—CO-Lys-Val-Lys-OH
Boc-Lys-Val-Lys-OH
Ac-Lys-Val-Lys-OH
Z-Lys-Val-Lys-OH
Fmoc-Lys-Val-Lys-OH
$C_8H_{17}$—$SO_2$-Lys-Val-Lys-OH
$C_{16}H_{33}$—$SO_2$-Lys-Val-Lys-OH
H-Lys-Val-Lys-$NH_2$
H-Lys-Val-Lys-OH
H-Lys-Thr-Lys-OH
H-Lys-Val-Lys-OOctyl
H-Lys-Val-Lys-OCetyl
H-Lys-Val-Lys-ORetinyl
H-Lys-Val-Lys-OTocopheryl
H-Lys-Val-Lys-OBn
H-Lys-Val-Lys-NH-Cetyl
H-Lys-Val-Lys-NH-Octyl
H-Lys-Val-Lys-NH-Bn The compounds of the present invention can be used in concentrations ranging between 0.5 and 5,000 ppm (w/w), preferably between 1 and 1000 ppm (w/w), in the cosmetic end product. The compounds of the present invention can be used as a solution, a dispersion, an emulsion or encapsulated in carriers such as macro-, micro- or nanocapsules, in liposomes or chylomicrons, or enclosed in macro-, micro- or nanoparticles or in microsponges or absorbed on powdered organic polymers, talc, bentonite and further inorganic carriers.

The compounds of the present invention can be used in any galenic form: O/W and W/O emulsions, milk, lotions, ointments, gelatinous and viscous, surfactant and emulsifying polymers, pomades, shampoos, soaps, gels, powders, sticks and pencils, sprays, body oils, face masks, plasters.

The compounds of the present invention as well as the cosmetic compositions containing same are used for skin care products, in particular against the formation and aggravation of wrinkles and against all consequences of natural or accelerated (sun rays, pollution) skin aging.

The following compositions constitute a further aspect of the present invention:

The tripeptide derivatives of general formula (I) can be composed with at least one additional skin care active. These compositions may contain additional dermatologically acceptable carriers as well.

Additional skin care actives: In a preferred embodiment, where the composition should be in contact with human horny tissue, the additional components should be suitable for application to horny tissue, i.e., when incorporated into the composition they are suitable for use in contact with human horny tissue without undue toxicity, incompatibility, instability, allergic response, and the like within the scope of sound medical judgment. The CTFA Cosmetic Ingredient Handbook, Second Edition (1992) describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments/colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropinyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., alpha or beta arbutin, hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins and derivatives thereof.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

Farnesol: The topical compositions of the present invention may contain a safe and effective amount of farnesol. Farnesol is a naturally occurring substance which is believed to act as a precursor and/or intermediate in the biosynthesis of squalene and sterols, especially cholesterol. Farnesol is also involved in protein modification and regulation (e.g., farnesylation of proteins), and there is a cell nuclear receptor which is responsive to farnesol.

Chemically, farnesol is [2E,6E]-3,7,11-trimethyl-2,6,10-dodecatrien-1-ol and as used herein "farnesol" includes isomers and tautomers of such. Farnesol is commercially available, e.g., under the names farnesol (a mixture of isomers from Dragoco, 10 Gordon Drive, Totowa, N.J., USA) and trans-trans-farnesol (Sigma Chemical Company, P.O. Box 14508, St. Louis, Mo., USA).

Phytantriol: The topical compositions of the present invention may contain a safe and effective amount of phytantriol. Phytantriol is the common name for the chemical known as 3,7,11,15-tetramethylhexadecane-1,2,3-triol. Phytantriol is useful, e.g., as a spider vessel/red blotchiness repair agent, a dark circle/puffy eye repair agent, sallowness repair agent, a sagging repair agent, an anti-itch agent, a skin thickening agent, a pore reduction agent, an oil/shine reduction agent, a post-inflammatory hyperpigmentation repair agent, a wound-treating agent, an anti-cellulite agent, and an agent for regulating skin texture, including wrinkles and fine lines.

Desquamation actives: A safe and effective amount of a desquamation active may be added to the compositions of the present invention, more preferably from about 0.1% to about 10%, even more preferably from about 0.2% to about 5%, also preferably from about 0.5% to about 4%, by weight of the composition. Desquamation actives enhance the skin appearance benefits of the present invention. For example, the desquamation actives tend to improve the texture of the skin (e.g., smoothness). One desquamation system that is suitable for use herein contains sulfhydryl compounds and zwitterionic surfactants and is described in U.S. Pat. No. 5,681,852 to Bissett, cited herein by reference. Another desquamation system that is suitable for use herein contains salicylic acid and zwitterionic surfactants and is described in U.S. Pat. No. 5,652,228 to Bissett, cited herein by reference. Zwitterionic surfactants such as described in these applications are also useful as desquamatory agents herein, with cetyl betaine being particularly preferred.

Anti-acne actives: The compositions of the present invention may contain a safe and effective amount of one or more anti-acne actives. Examples of useful anti-acne actives include resorcinol, sulfur, salicylic acid, benzoyl peroxide, erythromycin, zinc, etc. Further examples of suitable anti-acne actives are described in further detail in U.S. Pat. No. 5,607,980, issued to McAtee on Mar. 4, 1997.

Anti-wrinkle actives/anti-atrophy actives: The compositions of the present invention may further contain a safe and effective amount of one or more anti-wrinkle actives or anti-atrophy actives. Exemplary anti-wrinkle/anti-atrophy actives suitable for use in the compositions of the present invention include sulfur-containing D and L amino acids and their derivatives and salts, particularly the N-acetyl derivatives, a preferred example of which is N-acetyl-L-cysteine; thiols, e.g., ethane thiol; hydroxy acids (e.g., alpha-hydroxy acids such as lactic acid and glycolic acid or beta-hydroxy acids such as salicylic acid and salicylic acid derivatives such as the octanoyl derivatives), phytic acid, lipoic acid; lysophosphatidic acid, skin peel agents (e.g., phenol and the like), vitamin $B_3$ compounds and retinoids which enhance the horny tissue appearance benefits of the present invention, especially in regulating keratinous tissue condition, e.g., skin condition.

a) Vitamin $B_3$ compounds: The compositions of the present invention may contain a safe and effective amount of a vitamin $B_3$ compound. Vitamin $B_3$ compounds are particularly useful for regulating skin condition as described in co-pending U.S. application Ser. No. 08/834,010, filed Apr. 11, 1997 (corresponding to international publication WO 97/39733 A1, published Oct. 30, 1997). Exemplary derivatives of the foregoing vitamin $B_3$ compounds include nicotinic acid esters, including non-vasodilating esters of nicotinic acid (e.g., tocopheryl nicotinate), nicotinyl amino acids, nicotinyl alcohol esters of carboxylic acids, nicotinic acid N-oxide and niacinamide N-oxide.

b) Retinoids: The compositions of the present invention may also contain a retinoid. As used herein, "retinoid" includes all natural and/or synthetic analogs of vitamin A or retinol-like compounds which possess the biological activity of vitamin A in the skin, as well as the geometric isomers and stereoisomers of these compounds. The retinoid is preferably retinol, retinol esters (e.g., $C_2$ to $C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. Other suitable retinoids are tocopheryl retinoate [tocopherol ester of retinoic acid (trans- or cis-), adaptalene {6-[3-(1-adamantyl)-4-methoxyphenyl]-2-naphthoic acid}, and tazarotene (ethyl 6-[2-(4,4-dimethylthiochroman-6-yl)-ethinyl]nicotinate). Preferred retinoids are retinol, retinyl palmitate, retinyl acetate, retinyl propionate, retinal and combinations thereof. The compositions of the present invention may contain a safe and effective amount of the retinoid, such that the resultant composition is safe and effective for regulating horny tissue condition, preferably for regulating visible and/or tactile discontinuities in skin, more preferably for regulating signs of skin aging, even more preferably for regulating visible and/or tactile discontinuities in skin texture associated with skin aging.

(c) Hydroxy acids: The compositions of the present invention may contain a safe and effective amount of a hydroxy acid. Preferred hydroxy acids for use in the compositions of the present invention include salicylic acid and salicylic acid derivatives.

Peptides: Additional peptides, including but not limited to di-, tri-, tetra- and pentapeptides and derivatives thereof, may be included in the compositions of the present invention in amounts that are safe and effective. As used herein, "peptides" refers to both naturally occurring peptides and synthesized peptides and also includes peptide mimetics and metal complexes of "peptides". Also useful herein are naturally occurring and commercially available compositions that contain peptides.

Suitable dipeptides for use herein include carnosine (β-Ala-His). Suitable tripeptides for use herein include Gly-His-Lys, Arg-Lys-Arg and His-Gly-Gly. Preferred tripeptides and derivatives thereof include palmitoyl-Gly-His-Lys, which may be purchased as Biopeptide CL™ (100 ppm of palmitoyl-Gly-His-Lys commercially available from Sederma, France); peptide CK (Arg-Lys-Arg); peptide CK+(Ac-Arg-Lys-Arg-NH$_2$); and a copper complex of Gly-His-Lys or of His-Gly-Gly sold as lamin from Sigma (St. Louis, Mo., USA). Suitable tetrapeptides for use herein include peptide E, Arg-Ser-Arg-Lys. Examples of pentapeptides are matrixyl (palmitoyl-Lys-Thr-Thr-Lys-Ser) available from Sederma, France, and those described in WO 03/037933 (Pentapharm, Switzerland).

Antioxidants/radical scavengers: The compositions of the present invention may include a safe and effective amount of an antioxidant/radical scavenger. The antioxidant/radical scavenger is especially useful for providing protection against UV radiation which can cause increased scaling or texture changes in the stratum corneum and against other environmental agents which can cause skin damage.

Antioxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox™), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pidolate, nordihydroguaiaretic acid, bioflavonoids, curcumin, lysine, 1-methionine, proline, superoxide dismutase, silymarin, tea extracts, grape skin/seed extracts, melanin, and rosemary extracts may be used. Preferred antioxidants/radical scavengers are selected from tocopherol sorbate and other esters of tocopherol, more preferably tocopherol sorbate. For example, the use of tocopherol sorbate in topical compositions applicable to the present invention is described in U.S. Pat. No. 4,847,071, issued on Jul. 11, 1989 to Donald L. Bissett, Rodney D. Bush and Ranjit Chatterjee.

Chelators: The compositions of the present invention may also contain a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

Exemplary chelators that are useful herein are disclosed in U.S. Pat. No. 5,487,884, issued on Jan. 30, 1996 to Bissett et al., International Publication No. 91/16035, Bush et al., published on Oct. 31, 1995 and International Publication No. 91/16034, Bush et al., published on Oct. 31, 1995.

Preferred chelators useful in the compositions of the present invention are furildioxime, furilmonoxime, and derivatives thereof.

Flavonoids: The compositions of the present invention may optionally contain a flavonoid compound. Flavonoids are broadly disclosed in U.S. Pat. No. 5,686,082 and U.S. Pat. No. 5,686,367, both of which are herein incorporated by reference. Flavonoids suitable for use in the present invention are flavanones selected from unsubstituted flavanones, mono-substituted flavanones, and mixtures thereof; chalcones selected from unsubstituted chalcones, mono-substituted chalcones, di-substituted chalcones, tri-substituted chalcones, and mixtures thereof; flavones selected from unsubstituted flavones, mono-substituted flavones, di-substituted flavones, and mixtures thereof; one or more isoflavones; coumarins selected from unsubstituted coumarins, mono-substituted coumarins, di-substituted coumarins, and mixtures thereof; chromones selected from unsubstituted chromones, mono-substituted chromones, di-substituted chromones, and mixtures thereof; one or more dicoumarols; one or more chromanones; one or more chromanols; isomers (e.g., cis/trans-isomers) thereof and mixtures thereof. The term "substituted" as used herein means flavonoids, wherein one or more hydrogen atom has been independently replaced with hydroxyl, $C_1$-$C_8$ alkyl, $C_1$-$C_4$ alkoxyl, O-glycoside, and the like or a mixture of these substituents.

Examples of suitable flavonoids include, but are not limited to, unsubstituted flavanone, mono-hydroxy flavanones (e.g., 2'-hydroxy flavanone, 6-hydroxy flavanone, 7-hydroxy flavanone, etc.), mono-alkoxy flavanones (e.g., 5-methoxy flavanone, 6-methoxy flavanone, 7-methoxy flavanone, 4'-methoxy flavanone, etc.), unsubstituted chalcone (especially unsubstituted trans-chalcone), mono-hydroxy chalcones (e.g., 2'-hydroxy chalcone, 4'-hydroxy chalcone, etc.), di-hydroxy chalcones (e.g., 2',4-dihydroxy chalcone, 2',4'-dihydroxy chalcone, 2,2'-dihydroxy chalcone, 2',3-dihydroxy chalcone, 2',5'-dihydroxy chalcone, etc.), and tri-hydroxy chalcones (e.g., 2',3',4'-trihydroxy chalcone, 4,2',4'-trihydroxy chalcone, 2,2',4'-trihydroxy chalcone, etc.), unsubstituted flavone, 7,2'-dihydroxy flavone, 3',4'-dihydroxy naphthoflavone, 4'-hydroxy flavone, 5,6-benzoflavone, and 7,8-benzoflavone, unsubstituted isoflavone, daidzein (7,4'-dihydroxy isoflavone), 5,7-dihydroxy-4'-methoxy isoflavone, soy isoflavones (a mixture extracted from soy), unsubstituted coumarin, 4-hydroxycoumarin, 7-hydroxy coumarin, 6-hydroxy-4-methyl coumarin, unsubstituted chromone, 3-formyl chromone, 3-formyl-6-isopropyl chromone, unsubstituted dicoumarol, unsubstituted chromanone, unsubstituted chromanol, and mixtures thereof.

Preferred for use herein are unsubstituted flavanone, methoxy flavanones, unsubstituted chalcone, 2',4-dihydroxy chalcone, and mixtures thereof. More preferred are unsubstituted flavanone, unsubstituted chalcone (especially the trans-isomer), and mixtures thereof.

Anti-inflammatory agents: The anti-inflammatory agent enhances the skin appearance benefits of the present invention, e.g., such agents contribute to a more uniform and acceptable skin tone or color.

Steroidal anti-inflammatory agents, including but not limited to, corticosteroids such as hydrocortisone, hydroxyltriamcinolone, alpha-methyldexamethasone, dexamethasone phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the non-steroidal anti-inflammatory agents. The variety of compounds encompassed by this group is well-known to those skilled in the art. For detailed disclosure of the chemical structure, synthesis, side effects, etc. of non-steroidal anti-inflammatory agents, one may refer to standard texts, including Anti-Inflammatory and Anti-Rheumatic Drugs, K. D. Rainsford, Vol. I-III, CRC Press, Boca Raton, (1985), and Anti-Inflammatory Agents, Chemistry and Pharmacology, 1, R. A. Scherrer et al., Academic Press, New York (1974).

Specific non-steroidal anti-inflammatory agents useful in the compositions of the present invention include, but are not limited to:
1) the oxicams, such as piroxicam, isoxicam, tenoxicam, sudoxicam and CP-14, 304;
2) the salicylates, such as aspirin, disalcid, benorylate, trilisate, safapryn, solprin, diflunisal and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac and ketorolac;
4) the fenamates, such as mefenamic, meclofenamic, flufenamic, niflumic and tolfenamic acids;
5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen and tiaprofenic acid; and
6) the pyrazoles, such as phenylbutazone, oxyphenbutazone, feprazone, azapropazone and trimethazone.

Mixtures of these non-steroidal anti-inflammatory agents may also be employed as well as the dermatologically acceptable salts and esters of these agents. For example, etofenamate, a flufenamic acid derivative, is particularly useful for topical application. Of the non-steroidal anti-inflammatory agents, ibuprofen, naproxen, flufenamic acid, etofenamate, aspirin, mefenamic acid, meclofenamic acid, piroxicam and felbinac are preferred; ibuprofen, naproxen, ketoprofen, etofenamate, aspirin and flufenamic acid are more preferred.

Finally, so-called "natural" anti-inflammatory agents are useful in the methods of the present invention. Such agents may suitably be obtained as an extract by suitable physical and/or chemical isolation from natural sources (e.g., plants, fungi, by-products of microorganisms) or can be synthetically prepared. For example, candelilla wax, bisabolol (e.g., alpha bisabolol), aloe vera, plant sterols (e.g., phytosterol), Manjistha (extracted from plants of the genus *Rubia*, particularly *Rubia Cordifolia*) and *Guggal* (extracted from plants of the genus *Commiphora*, particularly *Commiphora Mukul*), kola extract, chamomile, red clover extract and sea alga extract may be used.

Additional anti-inflammatory agents useful herein include compounds of the liquorice (the plant genus/species *Glycyrrhiza glabra*) family, including glycyrrhetic acid, glycyrrhizic acid and derivatives thereof (e.g., salts and esters). Suitable salts of the foregoing compounds include metal and ammonium salts.

Anti-cellulite agents: The compositions of the present invention may also contain a safe and effective amount of an anti-cellulite agent. Suitable agents may include, but are not limited to, xanthine compounds (e.g., caffeine, theophylline, theobromine and aminophylline).

Skin-tanning actives: Dihydroxyacetone, which is also known as DHA or 1,3-dihydroxy-2-propanone, is a white to off-white, crystalline powder. The compound can exist as a mixture of monomers and dimers, with the dimers predominating in the solid crystalline state. Upon heating or melting, the dimers break down to yield the monomers. This conversion of the dimeric form to the monomeric form also occurs in aqueous solution. One further example is erythrulose, available from Pentapharm, Switzerland. DHA and erythrulose can be administered in combination.

Skin-lightening agents: Suitable skin-lightening agents comprise those known in the art, including kojic acid, arbutin, alpha-arbutin, ascorbic acid and derivatives thereof (e.g., magnesium ascorbyl phosphate or sodium ascorbyl phosphate) and extracts (e.g., mulberry extract, placental extract).

Skin-soothing and skin-healing actives: The compositions of the present invention may comprise a skin-soothing or skin-healing active. Skin-soothing or skin-healing actives suitable for use herein include panthenoic acid derivatives (including panthenol, dexpanthenol, ethyl panthenol), aloe vera, allantoin, bisabolol and dipotassium glycyrrhizinate.

Bisabolol: The topical compositions of the present invention may also contain a safe and effective amount of bisabolol. Bisabolol is a naturally occurring, unsaturated, monocyclic terpene alcohol having the following structure:

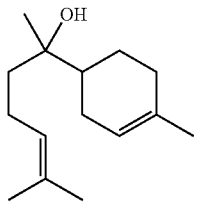

It is the primary active component of chamomile extract/oil. Bisabolol can be synthetic (d,1-alpha-isomer or (+/−)-alpha-isomer) or natural ((−)-alpha-isomer) in origin and can be used as essentially pure compounds or mixtures of compounds (e.g., extracts from natural sources such as chamomile). The alpha form of bisabolol (a-bisabolol) is used in a variety of cosmetic products as a skin conditioning or soothing agent. As used herein, "bisabolol" includes chamomile extract or oil and any isomers and tautomers of such. Suitable bisabolol compounds are commercially available as a natural material from Dragoco (Totowa, N.J., USA) under the product name alpha-bisabolol natural and as a synthetic material from Fluka (Milwaukee, Wis., USA) under the product name alpha-bisabolol.

Antimicrobial and antifungal actives: The compositions of the present invention may contain an antimicrobial or antifungal active. Such actives are capable of destroying microbes, preventing the development of microbes or preventing the pathogenic action of microbes. Preferred examples of actives useful herein include those selected from salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, 2,4,4'-trichloro-2'-hydroxy diphenyl ether, 3,4,4'-trichlorocarbanilide, octopirox, lidocaine hydrochloride, clotrimazole, miconazole, ketoconazole, neocycin sulfate and mixtures thereof.

Sunscreen actives: Exposure to ultraviolet light can result in excessive scaling and texture changes of the stratum corneum. Therefore, the compositions of the present invention may optionally contain a sunscreen active. As used herein, "sunscreen active" includes both sunscreen agents and physical sunblocks. Suitable sunscreen actives may be organic or inorganic.

Inorganic sunscreens useful herein include the following metallic oxides: titanium dioxide, zinc oxide, zirconium oxide, iron oxide and mixtures thereof.

Examples of organic sunscreens are 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethylaminobenzoic acid or aminobenzoate, 2-ethylhexyl-p-dimethylaminobenzoate, 2-phenylbenzimidazole-5-sulfonic acid, 2-(p-dimethylaminophenyl)-5-sulfonicbenzoxazoic acid, octocrylene, 2,2'-methylene-bis-[6-(2H-benzotriazol-2-yl)-4-(1,1,3,3-tetramethylbutyl)-phenol] available from Ciba SC as TINOSORB™ M, 2,4-Bis-[(4-(2-ethylhexyloxy)-2-hydroxy)-phenyl]-6-(4-methoxyphenyl)-1,3,5-triazin available from Ciba SC as TINOSORB™ S and mixtures of these compounds.

Also particularly useful in the compositions are sunscreen actives such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991. The sunscreen agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Preferred members of this class of sunscreens are 4-N,N-(2-ethylhexyl)methyl-aminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methyl-aminobenzoic acid ester with 4-hydroxydibenzoylmethane; 4-N,N-(2-ethylhexyl)methyl-aminobenzoic acid ester of 2-hydroxy-4-(2-hydroxyethoxy)benzophenone; 4-N,N-(2-ethylhexyl)-methylaminobenzoic acid ester of 4-(2-hydroxyethoxy)dibenzoylmethane; N,N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof. Exact amounts will vary depending upon the sunscreen or sunscreens chosen and the desired Sun Protection Factor (SPF).

Conditioning agents: The compositions of the present invention may contain a conditioning agent selected from humectants, moisturizers or skin conditioners. These materials include, but are not limited to, guanidine, urea, glycolic acid and glycolate salts (e.g., ammonium and quaternary alkyl ammonium), salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches, sugar and starch derivatives (e.g., alkoxylated glucose, fructose, glucosamine), hyaluronic acid, lactamide monoethanolamine, acetamide monoethanolamine, panthenol, allantoin and mixtures thereof. Also useful herein are the propoxylated glycerols described in U.S. Pat. No. 4,976,953, to Orr et al., issued on Dec. 11, 1990.

Also useful are various $C_1$-$C_{30}$ monoesters and polyesters of sugars and related materials. These esters are derived from a sugar or polyol moiety and one or more carboxylic acid moieties.

Preferably, the conditioning agent is selected from urea, guanidine, sucrose polyester, panthenol, dexpanthenol, allantoin and combinations thereof.

Dermatologically acceptable carriers: The topical compositions of the present invention also contain a dermatologically acceptable carrier. The phrase "dermatologically acceptable carrier", as used herein, means that the carrier is suitable for topical application to the horny tissue, has good aesthetic properties, is compatible with the actives of the present invention and any other components, and will not cause any untoward safety or toxicity concerns.

The carrier can be in a wide variety of forms. For example, emulsion carriers, including, but not limited to, oil-in-water, water-in-oil, water-in-oil-in-water, and oil-in-water-in-silicone emulsions, are useful herein.

A) Water-in-silicone emulsion
   Water-in-silicone emulsions contain a continuous silicone phase and a dispersed aqueous phase.
B) Oil-in-water emulsions
   Other preferred topical carriers include oil-in-water emulsions having a continuous aqueous phase and a hydrophobic, water-insoluble phase ("oil phase") dispersed therein. Examples of suitable oil-in-water emulsion carriers are described in U.S. Pat. No. 5,073,371 issued to D. J. Turner et al. on Dec. 17, 1991 and U.S. Pat. No. 5,073,372 issued to D. J. Turner et al. on Dec. 17, 1991.

EXAMPLES

The following examples should illustrate the invention without limiting its scope. The following abbreviations are used in the text and in Examples 1-7:
AcOH: Acetic acid
AB: Antibody
Boc: tert.-Butyloxycarbonyl
BSA: Bovine serum albumine
Dab: 2,4-Diaminobutyric acid
Dap: 2,3-Diaminopropionic acid
DBU: 1,8-Diazabicyclo[5,4,0]undec-7-ene(1, 5-5)
FCS: Foetal calf serum
TFA: Trifluoroacetic acid
Gly: Glycine
Hse: Homoserine
Ile: Isoleucine
MEM: Minimal essential medium
NEAA: Non essential amino acids
Nle: Norleucine
Nva: Norvaline
Orn: Ornithine
Palm: Palmitoyl
PBS: Phosphate buffered saline
Pe: Petroleum ether
RT: Room temperature
tBu: tert.-Butyl
tBuGly: tert.-Butylglycine
TBTU: O-(Benzotriazol-1-yl)-N,N,N',N',-tetramethyluronium-tetrafluoroborate
TGFβ1: Transforming growth factor-β1

Example 1

Determination of the stimulation of collagen type 1 synthesis in fibroblast cell cultures by treatment with the tripeptide derivatives of the present invention Type I collagen of in-vitro cultured skin fibroblasts was detected with an ELISA (Enzyme-Linked Immunosorbent Assay). The increase in the collagen production of the cells was quantified in the presence of the peptidic actives by using this method.

Human skin fibroblasts were isolated from foreskin and bred in culture medium.

After 72 h of incubation with the corresponding peptides (actives) the quantitative determination was performed using an antibody specific for collagen I Material:

| Culture Medium: | Test medium: |
|---|---|
| MEM | MEM |
| 10% FCS | no FCS |
| 100 IU/ml penicillin | 100 IU/ml penicillin |
| 0.1 mg/ml streptomycin | 0.1 mg/ml streptomycin |
| 1 mM NEAA | 1 mM NEAA |
| 1 mM Na pyruvate | 1 mM Na pyruvate |
| 2 mM L-glutamine | 2 mM L-glutamine |
| 20 mM HEPES buffer | 20 mM HEPES buffer |
| Washing buffer: | Milk solution: |
| 0.05 M Tris, pH 8.5 | washing buffer |
| 0.15 M NaCl | 5% milk powder |
| 0.1% BSA | |
| 0.1% Tween-20 | |
| AB dilution solution: | Substrate solution: |
| 50 ml Superblock (37515; Pierce) | 1 ImmunoPure ® OPD tablet (34006; Pierce) |
| 450 ml $H_2O$ | 9 ml $H_2O$ |
| 0.05% Tween | 1 ml stable peroxide substrate buffer, 10x (34062; Pierce) |

The 1$^{st}$ AB (MAB1340; Chemicon) and the 2$^{nd}$ AB (31430; Socochim S.A.) are diluted 1/500 with AB dilution solution.

Method:

The fibroblasts are incubated until confluent at a density of approx. 5000 cells per well in 96 well-plates in culture medium (37° C./5% $CO_2$) for 3 days. The medium is replaced with test medium with three different concentrations of test substance in triplicate. The following controls are tested on each plate:

| Negative controls: | Positive controls: |
|---|---|
| A) | A) |
| with cells without 1$^{st}$ AB; with 2$^{nd}$ AB | with cells with 1$^{st}$ and 2$^{nd}$ AB |
| B) | B) |
| without cells with 1$^{st}$ and 2$^{nd}$ AB | with cells with 1$^{st}$ and 2$^{nd}$ AB with 10 ng/ml TGF-β1 |
| C) For each peptide a well without cells is tested to exclude the unspecific binding of both AB. | |

After incubation of the plates for further 72 hours, the precipitated collagen I is detected and quantified according to the following protocol:

discard medium and wash with 200 μl/well of PBS fix with 100 μl/well of methanol for 15 min at RT/shaker 600 rpm discard methanol and block with 200 μl/well of milk solution for 30 min at RT/shaker 600 rpm discard milk solution and incubate with 100 μl/well of the 1$^{st}$ AB dilution for 2 h at RT/shaker 600 rpm discard 1$^{st}$ AB dilution and wash 3× with 200 μl/well of washing buffer incubate with 100 μl/well of the 2$^{nd}$ AB dilution for 3 h at RT/shaker 600 rpm discard 2$^{nd}$ AB dilution; wash 3× with 200 μl/well of washing buffer and 1× with 100 μl/well of PBS add 100 μl/well of substrate solution for 20 min at RT/shaker 600 rpm stop the reaction with 50 μl/well of H$_2$SO$_4$ (2M) and measure at 492 nm.

TABLE 1

Collagen stimulation by ELISA:

| No | Substance | Conc./ [μmol/L] | % Stimulation |
|---|---|---|---|
| | Control without active | — | 0 |
| | Reference compound A (Elaidoyl-Lys-Phe-Lys-OH *2AcOH) | 0.01/ 20.0 | 23 43 |
| 1 | Elaidoyl-Lys-Thr-Lys-OH *2AcOH | 0.01 | 36 |
| 2 | Elaidoyl-Lys-Val-Lys-OH *2AcOH | 0.01 | 30 |
| 3 | Palm-Lys-Thr-Lys-OH *2AcOH | 1.56 | 35 |
| 4 | Palm-Lys-Val-Lys-OH *2AcOH | 25.0 | 104 |
| 5 | Palm-Dap-Val-Lys-OH *2TFA | 50 | 35 |
| 6 | Palm-Dap-Val-Lys-OH *2TFA | 50 | 48 |
| 7 | Myristoyl-Lys-Val-Lys-OH *2TFA | 100 | 61 |
| 8 | Palm-Lys-Val-Orn-OH *2TFA | 25 | 31 |
| 9 | Palm-Lys-Ile-Lys-OH *2TFA | 25 | 38 |
| 10 | H$_{29}$C$_{14}$—NH—CO-Lys-Val-Lys-OH *2TFA | 50 | 63 |
| 11 | H$_{33}$C$_{16}$—NH—CO-Lys-Val-Lys-OH*2TFA | 50 | 41 |
| 12 | H$_{37}$C$_{18}$—NH—CO-Lys-Val-Lys-OH*2TFA | 50 | 25 |
| 13 | Palm-Lys-Val-Dap-OH *2TFA | 100 | 154 |
| 14 | Palm-Lys-Val-Dab-OH *2TFA | 25 | 60 |
| 15 | Palm-Arg-Val-Arg-OH *2TFA | 50 | 49 |

Example 2

Formulation of an Ointment

Method: Ingredients 1-5 (A) are heated to 70° C. Ingredients 6-7 (B) are heated to 75° C. Under stirring B is added to A, cooled to 50° C., homogenized and cooled to 30° C. Afterwards, ingredients 8-9 (C) and ingredient 10 (D) are added one after the other and the mixture is stirred cold.

| No. | Ingredient | | % w/w |
|---|---|---|---|
| 1 | (A) | Tego Care 450 | 3.00 |
| 2 | | Cetearyl alcohol | 2.25 |
| 3 | | Glyceryl stearate | 2.25 |
| 4 | | Cetiol 868 | 10.00 |
| 5 | | Squalane | 5.00 |
| 6 | (B) | Deionized water | 66.995 |
| 7 | | Sodium hyaluronate | 5.00 |
| 8 | (C) | Glycerin | 5.00 |
| 9 | | Phenonip | 0.5 |
| 10 | (D) | Palm-Lys-Val-Lys-OH | 0.005 |

Example 3

Formulation of a Gel

Method: Ingredients 2-6 (A) are dissolved one after the other in deionized water. The pH is adjusted to 6.0 with ingredient 7 (B), whereupon ingredient 8 (C) is added.

| No. | Ingredient | | % w/w |
|---|---|---|---|
| 1 | (A) | Deionized water | 192.095 |
| 2 | | 1,3-Butanediol | 5.00 |
| 3 | | Phenonip | 0.50 |
| 4 | | Abil B 8843 | 1.50 |
| 5 | | Carboxymethyl Cellulose | 0.15 |
| 6 | | Carbopol Ultrez 10 | 0.75 |
| 7 | (B) | NaOH | |
| 8 | (C) | Palm-Lys-Val-Lys-OH | 0.005 |

Examples 4-8

The following embodiments 4-8 describe the synthesis of the compounds of formula (I) of the present invention and of salts of such compounds. The eluates and products obtained according to the examples are analysed using proton NMR, HPLC electrospray MS or microanalysis. The compounds can be manufactured according to known methods described hereinafter (general instructions from M. Bodanszky "The Practice of Peptide Synthesis", Springer, 2$^{nd}$ Edition, 1994). Accordingly, the amino acid, e.g. lysine, is bound to a resin at the carboxy terminus in a solid-phase synthesis, whereby its amino group is protected by a protective group, e.g. by the Fmoc protective group. The side chain is protected with, e.g., Boc or t-butyl. If necessary, the protective groups are selectively split off in order to link up the further amino acid derivatives with the reagents commonly used in peptide synthesis until the desired chain is completely built up. Afterwards, the peptide is split off from the resin at the carboxy terminus and the crude peptide is precipitated by instillation into an appropriate solvent mixture. The mixture is purified by HPLC, optionally exchanged in the opposite ions and the substance is lyophilized.

Example 4

Elaidoyl-Lys-Thr-Lys-OH *2TFA

The protective peptide is built on 1.00 g (0.78 mmol) of H-Lys(Boc)-2-chlorotrityl resin using Fmoc-Thr(tBu)-OH, Fmoc-Lys(Boc)-OH and elaidoyl-OSu. The resin is treated for 30 min with 8 ml of TFA 95% and the solution is poured in drops into 100 ml of Et$_2$O. The precipitate is sucked off, washed, purified by preparative HPLC after drying and lyophilized.

Yield: 73 mg (0.097 mmol, 12%)

Example 5

H-Lys-Thr-Lys-OH *3TFA

The protective peptide is built on 3.00 g (2.58 mmol) of H-Lys(Boc)-2-chlorotrityl resin using Fmoc-Thr(tBu)-OH and Z-Lys(Z)—OH. The resin is treated for 30 min with 20 ml of TFA 95% and the solution is poured in drops into 400 ml of $^t$BuOMe:PE=1:1. The precipitate is sucked off, washed and purified by prep. HPLC after drying.

The partially protected peptide is dissolved in 50 ml of dioxan:water=4:6, mixed with 200 mg Pd/C and 3 Eq TFA and reduced for 5 h under H$_2$ atmosphere. The mixture is filtered through Celite, rotated, purified by prep. HPLC and lyophilized.

Example 6

Palm-Lys-Val-Lys-OH *2AcOH

The protective peptide is built on 1.00 g (0.80 mmol) of H-Lys(Boc)-2-chlorotrityl resin using Fmoc-Val-OH, Fmoc-Lys(Boc)-OH and Palm-OSu. The resin is treated for 30 min with 8 ml of TFA 95% and the solution is instilled in 100 ml of Et$_2$O. The precipitate is sucked off, washed and purified by prep. HPLC after drying. The substance is diluted in 30 ml of dioxan:water=4:6, treated overnight with 2.0 g of BioRad resin (acetate form), filtered, rotated and lyophilized. Yield: 110 mg (0.15 mmol, 19%)

Example 7

H-Lys-Val-Lys-NH-Cetyl *3TFA

The protective peptide is built on 13.5 g (10.8 mmol) of H-Lys(Boc)-2-chlorotrityl resin using Fmoc-Val-OH and Boc-Lys(Boc)-OH. The resin is treated for 3*10 min with 80 ml of TFA 1% in methylene chloride and the solution is neutralized with pyridine:methanol solution and purified by prep. HPLC.

Yield: Boc-Lys(Boc)-Val-Lys(Boc)-OH 4.66 g (6.915 mmol, 64%)

84 µl (0.441 mmol) of DIPEA, 78.5 mg (0.245 mmol) of TBTU and 59.1 mg (0.245 mmol) of cetyl amine are added to 150 mg (0.223 mmol) of Boc-Lys(Boc)-Val-Lys(Boc)-OH in 5 ml of DMF. After 30 min the reaction solution is submitted to an aqueous extraction and the residue from the organic phase is treated for 30 min with TFA 95% and purified by prep. HPLC.

Yield: H-Lys-Val-Lys-NH-Cetyl *3TFA 48.2 mg (0.051 mmol, 23%)

Example 8

H-Lys-Val-Lys-O-Octyl *3TFA 10 ml of octanol are cooled to −10° C. and 75 µl of SOCl$_2$ (1.03 mmol) are carefully added. After 10 min 150 mg (0.223 mmol) of Boc-Lys(Boc)-Val-Lys(Boc)-OH are added and the mixture is stirred for 3 days. The product is obtained by purification over prep. HPLC.

Yield: H-Lys-Val-Lys-O-Octyl *3TFA 165.6 mg (0.200 mmol, 90%)

The invention claimed is:
1. Tripeptide derivatives of general formula I

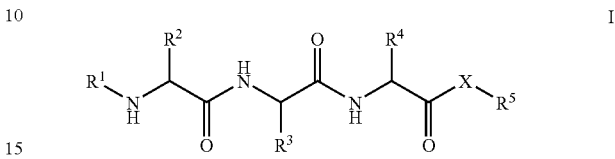

wherein
R$^1$ represents —C(O)—R$^6$,
R$^2$ and R$^4$ represent (CH$_2$)$_n$—NH$_2$
n equals 1-4,
R$^3$ represents linear or branched C$_1$-C$_4$-alkyl optionally substituted by hydroxy,
R$^5$ represents hydrogen, (C$_1$-C$_{24}$)-alkyl or optionally substituted C$_2$-C$_{24}$-alkenyl,
R$^6$ represents (C$_1$-C$_{24}$)-alkyl or optionally substituted C$_2$-C$_{24}$-alkenyl, and
X represents oxygen (—O—) or —NH—; or
XR$^5$ with X=O also represents the esters of α-tocopherol, tocotrienol or retinol.
2. Compounds according to claim 1, thereby characterized that R$^5$ represents hydrogen.
3. Compounds according to claim 1, thereby characterized that the compounds of formula I together with acids can form mono- or polyvalent, homogeneous or mixed salts, preferably with inorganic acids, or with appropriate organic aliphatic saturated or unsaturated carboxylic acids, or with aromatic carboxylic acids, or with aromatic-aliphatic carboxylic acids, or with heteroaromatic carboxylic acids, or with aliphatic or aromatic sulfonic acids, preferably with acetic acid, trifluoroacetic acid and/or lactic acid.
4. Compounds according to claim 1, thereby characterized that they are present as pure isomers or mixtures of different isomers, and as mixtures of rotamers.
5. Compounds of formulas
Elaidoyl-Lys-Val-Lys-OH
Elaidoyl-Lys-Thr-Lys-OH
Palm-Lys-Thr-Lys-OH
Palm-Lys-Val-Lys-OH
Palm-Orn-Val-Lys-OH
Palm-Orn-Val-Dab-OH
Palm-Orn-Val-Dap-OH
Palm-Dab-Val-Lys-OH
Palm-Dab-Val-Dab-OH
Palm-Dab-Val-Dap-OH
Palm-Dap-Val-Lys-OH
Palm-Dap-Val-Dab-OH
Palm-Dap-Val-Dap-OH
Palm-Arg-Val-Lys-OH
Palm-Arg-Val-Dab-OH
Palm-Arg-Val-Dap-OH
Palm-Lys-Val-Lys-OH
Palm-Lys-Val-Orn-OH
Palm-Lys-Val-Dab-OH
Palm-Lys-Val-Dap-OH
Palm-Lys-Val-Arg-OH
Palm-Lys-Leu-Lys-OH Palm-Lys-Ile-Lys-OH
Palm-Lys-Ile-Dab-OH
Palm-Lys-Nva-Dab-OH
Palm-Lys-tBuGly-Dab-OH
Palm-Lys-Leu-Dab-OH
Palm-Lys-Ile-Dap-OH
Palm-Lys-Nva-Dap-OH
Palm-Lys-tBuGly-Dap-OH
Palm-Lys-Leu-Dap-OH
Palm-Lys-Nle-Lys-OH
Palm-Lys-Ala-Lys-OH
Palm-Lys-Ser-Lys-OH
Palm-Lys-Hse-Lys-OH
Palm-Arg-Val-Arg-OH
Pentadecanoyl-Lys-Val-Dab-OH
Pentadecanoyl-Lys-Val-Dap-OH
Heptadecanoyl-Lys-Val-Dab-OH
Heptadecanoyl-Lys-Val-Dap-OH
Myristoyl-Lys-Val-Lys-OH
Myristoyl-Lys-Val-Dab-OH
Myristoyl-Lys-Val-Dap-OH
Lauroyl-Lys-Val-Lys-OH
Caprinoyl-Lys-Val-Lys-OH
Stearoyl-Lys-Val-Lys-OH
Stearoyl-Lys-Val-Dab-OH
Stearoyl-Lys-Val-Dap-OH
Oleolyl-Lys-Val-Lys-OH
Palm-Lys-Val-Dab-OMe
Palm-Lys-Val-Dab-OOctyl
Palm-Lys-Val-Dab-OCetyl
Palm-Lys-Val-Dab-NH$_2$
Palm-Lys-Val-Dab-NHBu
Palm-Lys-Val-Dab-NHOctyl
Palm-Lys-Val-Dab-NHCetyl
Palm-Lys-Val-Dap-OMe
Palm-Lys-Val-Dap-OOctyl
Palm-Lys-Val-Dap-OCetyl
Palm-Lys-Val-Dap-NH$_2$
Palm-Lys-Val-Dap-NHBu
Palm-Lys-Val-Dap-NHOctyl
Palm-Lys-Val-Dap-NHCetyl
$C_{14}H_{29}$—NH—CO-Lys-Val-Lys-OH
$C_{14}H_{29}$—NH—CO-Dab-Val-Dab-OH
$C_{14}H_{29}$—NH—CO-Lys-Ile-Dab-OH
$C_{14}H_{29}$—NH—CO-Lys-Val-Dap-OH
$C_{14}H_{29}$—NH—CO-Arg-Val-Arg-OH
$C_{14}H_{29}$—NH—CO-Dab-Val-Dap-OH
$C_{14}H_{29}$—NH—CO-Lys-Ile-Dap-OH
$C_{14}H_{29}$—NH—CO-Lys-Val-Dab-OH
$C_{14}H_{29}$—NH—CO-Dap-Val-Dap-OH
$C_{16}H_{33}$—NH—CO-Lys-Val-Lys-OH
$C_{18}H_{37}$—NH—CO-Lys-Val-Lys-OH
Boc-Lys-Val-Lys-OH
Ac-Lys-Val-Lys-OH
Z-Lys-Val-Lys-OH
Fmoc-Lys-Val-Lys-OH
$C_8H_{17}$—SO$_2$-Lys-Val-Lys-OH
$C_{16}H_{33}$—SO$_2$-Lys-Val-Lys-OH
H-Lys-Val-Lys-NH$_2$
H-Lys-Val-Lys-OH
H-Lys-Thr-Lys-OH
H-Lys-Val-Lys-OOctyl
H-Lys-Val-Lys-OCetyl
H-Lys-Val-Lys-ORetinyl
H-Lys-Val-Lys-OTocopheryl
H-Lys-Val-Lys-OBn
H-Lys-Val-Lys-NH-Cetyl
H-Lys-Val-Lys-NH-Octyl
H-Lys-Val-Lys-NH-Bn
and the acid addition salts thereof.

* * * * *